US005593849A

United States Patent [19]
Roy

[11] Patent Number: 5,593,849
[45] Date of Patent: Jan. 14, 1997

[54] **METHOD FOR DETECTING ANTIBODY AGAINST *STAPHYLOCOCCUS AUREUS* FOR REPLICATION PROTEIN B SEQUENCE 275-290 AND ARG-LYS-LEU IN HUMAN BODY FLUIDS**

[76] Inventor: Benjamin F. Roy, Suite 102, 69 Trinity Pl., Albany, N.Y. 12202

[21] Appl. No.: 201,081

[22] Filed: Feb. 24, 1994

Related U.S. Application Data

[63] Continuation of Ser. No. 76,727, Jun. 14, 1993.
[51] Int. Cl.$^6$ ................................................. G01N 33/569
[52] U.S. Cl. ........................... 435/7.33; 435/7.1; 435/7.9; 435/7.92; 435/7.94; 435/975; 436/531; 530/326; 530/327; 530/330; 530/331; 530/825
[58] Field of Search ............................. 435/7.33, 5, 7.31, 435/7.22, 7.32, 7.34, 7.35, 7.36, 7.37, 7.95, 975, 882, 883, 884, 7.1, 7.7, 7.9, 7.92–7.94; 530/326, 327, 330, 331, 825; 436/531, 532

[56] References Cited

U.S. PATENT DOCUMENTS 4,868,107  9/1989  Roy, III ................................... 435/7.95

OTHER PUBLICATIONS

Sigma Chemical Company Catalogue of Biochemicals, Organic Compounds for Research and Diagnostic Reagents, (St. Louis, MO), p. 2153, 1992.
Adelmann et al, "Molecular Mimicry and the Autoimmune Response to the Peripheral Nerve Myelin PO Glycoprotein", Neurochem. Res, 17(9):887–891 (Sep. 1992).
Cunningham et al, "Human and Murine Antibodies Cross–Reactive with Streptococcal M. Protein and Myosin Recognize the Sequence Gln–Lys–Ser–Gln in Protein M", J. Immunol, 143(8)2677–2683 (Oct. 15, 1989).
Roy et al., "Anti–β–endorphin Immunoglobulin G in Humans", *Proc. Natl. Acad. Sci. USA* 83 (Nov. 1986) 8739–8743.
Roy et al., "Antisomatostatin IgG in Major Depressive Disorder," *Arch. Gen. Psychiatry* 45 (Oct. 1988): 924–928.
Roy et al., "Human Antiidiotypic Antibody Against Opiate Receptors," *Anals of Neurology* 24 (Jul. 1988):57–103.
McKenzie et al., "The Nucleotide Sequence of pUB110: Some Salient Features in Relation to Repulication and Its Regulation," *Plasmid* 15 (1986):93–103.
Bouia et al., "Structural Organization of PLP1, a Cryptic Plasmid from *Lactobacillus plantarum* CCM 1094," *Plasmid* 22 (1989):185–192.
Cowman and Galatis, "*Plasmodium Falciparum*: The Calmodulin Gene Is Not Amplified or Overexpressed in Chloroquine Resistant or Sensitive Isolates," *Experimental Parasitology* 73 (1991): 269–275.,
Schweizer et al., "The Pentafunctional FAS1 Gene of Yeast; Its Nucleotide Sequence And Order of the Catalytic Domains," *Mol Gne. Genet* 203 (1986): 479–486.

Sommer et al., "The Murine GABAA$_A$ Receptor δ–Subunit Gene: Structure and Assignment to Human Chromosome 1," *DNA and Cell Biology* 9 (1990): 561–568.
Schwimmbeck et al., "Molecular Mimicry and Myasthenia Gravis," *Department of Immumiology, Research Institute of Scripps Clinic* (1989): 1174–1180.
Elkon et al., "Lupus Autoantibodies Target Ribosomal P Proteins," *J. Exp. Med* 162 (1985): 459–471.
Bonfa et al., "Association Between Lupus Psychosis and Anti–Ribosomal P Protein Antibodies," *The New England Journal of Medicine* 317 (1987): 265–271.
Fujita et al., "The Primary Structure of Phosepoenolpyruvate Carboxylase of *Escherichia coli*. Nucleotide Sequence of the ppc Gene and Deduce Amino Acid Sequence," *J. Biochem* 95 (1984): 909–916.
Kraus and Beachey, "Renal Autoimmune Epitope of Group A Streptococci Specified by M Protein Tetrapeptide Ile–Arg–Leu–Arg," *Proc. Natl. Acad. USA* 85 (Jun. 1988): 4516–4520.
Jackson and Iandolo, "Sequence of the Exfoliative Toxin B Gene of *Straphyloccus aureus*," *Journal of Bacteriology* (Aug. 1986): 726–728.
Baer et al., "DNA Sequence and Expression of the B95–8Epstein–Barr Virus Genome," *Nature* 310 (1984): 207–211.
Kakidani et al., "Cloning and Sequence Analysis oc cDNA for Procine β–neo–endorphin/dynorphin Precursor," *Nature* 298 (15 Jul. 1982): 245–249.
Noda et al., "Cloning and Sequence Analysis of cDNA for Bovine Adrenal Preproenkealin," *Nature* 295 (21 Jan. 1982): 202–206.
Nakanishi et al., "Nucleotide Sequence of Cloned cDNA for Bovine Corticotropin–β–lipoytopin Precursor," *Nature* 278 (29 Mar. 1979): 423–427.
Neu et al., "Cardiac Myosin Induces Myocarditis in Gnetically Predispose Mice," *The Journal of Immunology* 139 (1 Dec. 1987): 3630–3636.
Hollingshead et al., "Complete Nucleotide Sequence of Type 6 M Protein of the Group A *Streptococcus*," *The Journal of Biological Chemistry* 261 (5 Feb. 1986): 1677–1686 Relation to Repulication and Its Regulation, *Plasmid* 15 (1986): 93–103.
Bonfa et al., "Clinical and Serologic Associations Of The Antiribosomal P Protein Antibody," *Arthritis and Rheumatism* 29 Aug. 1986): 981–985.
Sikela and Hahn, "Screening an Expression Library With a Ligand Probe: Isolation and Sequence of a cDNA Corresponding to a Brain Calmodulin–binding Protein," *Proc. Natl. Acad. Sci. USA* 84 (May 1987): 3038–3042.

(List continued on next page.)

*Primary Examiner*—Christine M. Nucker
*Assistant Examiner*—Jeffrey Stucker
*Attorney, Agent, or Firm*—Cammarata & Grandinetti

[57] ABSTRACT

This is an immunochemical assay that uses enzyme-linked immunosorbence to detect the presence of antibodies against environmental protein sequences that mimic the human opioid peptide dynorphin in samples of human body fluid. The assay makes it possible to correlate and diagnose psychobiological or medical disorders related to alterations in the normal levels of dynorphin peptides or their receptors.

4 Claims, 7 Drawing Sheets

OTHER PUBLICATIONS

Fliegel et al., "Amino Acid Sequence of Rabbit Fast–twitch Skeletal Muscle Calsequestrin Deduced From cDNA and Peptide Sequencing," *Proc. Natl. Acad. Sci. USA* 84 (Mar. 1987): 1167–1171.

Bennet and Kennedy, "Deduced Primary Structure of the β Subunit of Brain Tyupe II $Ca^{2+}$/calmodulin–dependent Protein Kinase Determined by Molecular Cloning," *Proc. Natl. Acad. Sci. USA* 84 (Apr. 1987): 1794–1798.

Krystal et al., "Sequential Mutations in Hemagglutinins of Influenza B Viorus Isolates: Definition of Antigenic Domains," *Proc. Natl. Acad. Sci. USA* 80 (Jul. 1983): 4527–4531.

Fujinami and Oldstone, "Amino Acid Homology Between the Encephalitogenic Site of Myelin Basic Protein and Virus: Mechanism for Autoimmunity,:" *Science* 230 (1985) 1043–1045.

Huang et al., "Molecular Cloning and Amino Acid Sequence of Brain L–glutamate Decarboxylase," *Proc. Natl. Acad. Sci. USA* 87 (Nov. 1990): 8491–8495.

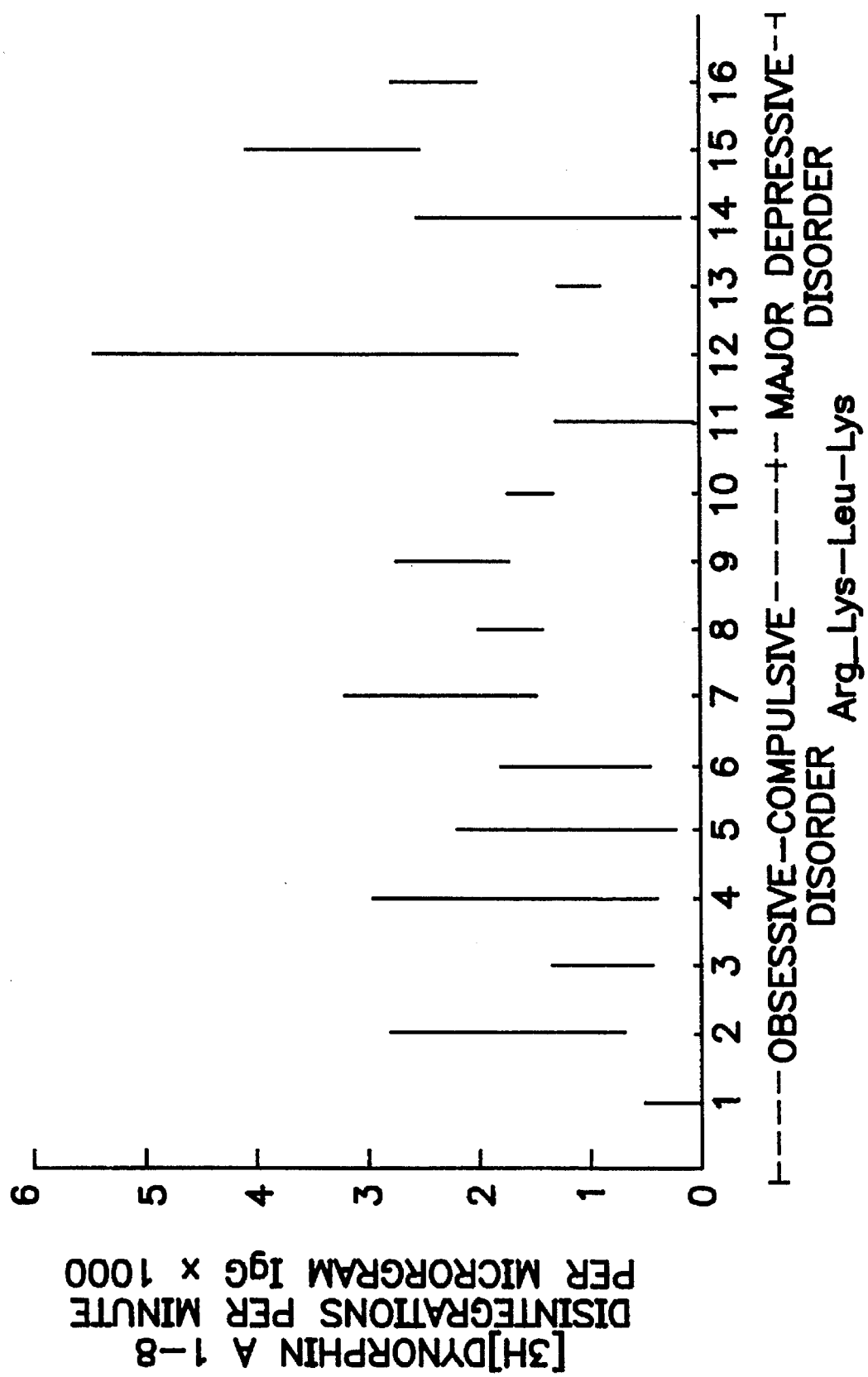

METHOD FOR DETECTING ANTIBODY AGAINST *STAPHYLOCOCCUS AUREUS* FOR REPLICATION PROTEIN B SEQUENCE 275-290 AND ARG-LYS-LEU IN HUMAN BODY FLUIDS

This application is a continuation of application Ser. No. 08/076,727 filed on Jun. 14, 1993.

BACKGROUND OF THE INVENTION

1. Field of the Invention

The present invention relates to immunochemical assays. More particularly, the present invention relates to enzyme-linked immunosorbent assay (ELISA) for detecting, in a sample of human body fluid, the presence of antibodies having binding affinity for (1) *Staphylococcus aureus* REPB 275–290 or other homologous bacterial REPB proteins and (2) Arg-Lys-Leu-Lys (SEQ ID NO: 1) bacterial or viral proteins that mimic the N-terminal and C-terminal human opioid peptide dynorphin A 1–17, respectively.

2. Description of Related Art

An immune response can be specific for restricted sequences of immunogenic proteins (epitopes) as small as four amino acids in length. Identical epitopes can be present on proteins from organisms as different as plants, bacteria, viruses, parasites, fungi, and humans. Thus, by chance, unrelated proteins may display areas of sequence or conformational homology (molecular mimicry). Repeated exposure to the same epitope on disparate and seemingly inconsequential environmental antigens can result in sensitization to, and loss of immune tolerance for, similar epitopes on host proteins. Eventually the immune response to the epitope may precipitate disease. Because the epitope is the target, the organism that initiated the cascade need no longer be present for the development of disease. If there is significant immunogenicity and cross-reactivity, the immune response to the environmental epitope may become misdirected against its human counterpart.

Molecular mimicry is important to the development of epitope-specific autoimmunity. For example, a six amino acid peptide shared by myelin basic protein and hepatitis virus polymerase causes experimental autoimmune encephalomyelitis in rabbits. This correlates with the development of clinical autoimmune encephalitis for myelin basic protein in humans after immunization with Semple vaccine, a preparation of rabies-infected animal tissue. A sequence shared by coxsackie B3 virus and myosin causes myocarditis in mice. This fits observations of clinical myocarditis in humans following infection with coxsackie virus.

Alterations in serum immunoglobulins and proteins associated with inflammation, and elevated antiviral titers point to an active infectious or autoimmune etiology of psychiatric disorders, but are not always demonstrated. Epidemiological surveys to link specific disorders to specific viral infections are provocative, but nonconclusive.

Despite this finding, psychiatric disorders have clinical and epidemiological association with infection. Moreover, infections characterized by consistent psychiatric sequelae exhibit molecular mimicry of host proteins, cross-reactive autoimmunity (i.e., epitope-specific autoimmunity), induction of idiotypic networks, and, in some cases, alterations of central neurotransmitters. This raises the consideration that the psychiatric sequelae might be a consequence of these factors.

Streptococcal infection is a prototypic cause of epitope-specific autoimmunity for heart, kidney, and brain. Disease may occur despite elimination of *Streptococcus pyogenes* from the body. Streptococcal infections are also associated with psychiatric sequelae. Prior to effective treatment for rheumatic fever schizophrenic-like symptoms appeared either during acute illness or many years after resolution of the disease. This led to hypotheses using rheumatic fever as a paradigm for an infectious origin of schizophrenia.

Despite modern treatment, rheumatic fever continues to present an array of psychiatric sequelae. Obsessive-compulsive disorder (OCD) occurs with Sydenham's chorea. Sydenham's chorea is a neurological disorder seen in 20 percent of the cases of rheumatic fever. Sydenham's chorea is a consequence of an autoimmune response for basal ganglia proteins that cross-react with Streptococci. Clinical obsessiveness is noted in half the cases of Sydenham's chorea. This exceeds the 0.4 percent prevalence for OCD in adolescence. Outbreaks of rheumatic fever in the midwest and Pennsylvania were characterized by a high incidence of OCD with significant obsessional scores on the Yale-Brown Obsessional Inventory and the Leyton Obsessional Inventory.

Like Sydenham's chorea primary OCD is linked to abnormalities of the basal ganglia. Furthermore, OCD shows genetic linkage to Gilles de la Tourette's syndrome, a basal ganglia disorder associated with obsessive symptoms.

The principal neuropeptides of the basal ganglia include dynorphins. Opiates have regulatory influence on serotonergic nuclei of the median raphe which send inhibitory projections to the basal ganglia. The possibility that dynorphin may be altered in OCD is raised by depletion of dynorphin in the striatum of patients with Gilles de la Tourette's syndrome.

There are three main branches of opiate peptides. Pro-opiomelanocortin, a pituitary peptide, is the parent peptide for beta-endorphin, corticotropin (ACTH), and alpha-melanocortin (MSH). Proenkephalin is present in both the adrenal gland and brain and is the precursor for methionine and leucine enkephalins, while prodynorphin is present in cortex and is the precursor for dynorphin peptides and neo-endorphins.

Opioid peptides are ubiquitous antigens produced by vegetables, parasites, bacteria, and vertebrates. As a result, sensitization to opioid peptides as environmental antigens might induce cross-reactive immunity for endogenous opioid peptides. Alterations in opioid peptides are implicated in the pathogenesis of a number of psychiatric disorders. There is the chance that epitope-specific autoimmunity for these peptides may contribute to these alterations.

Some patients with major depressive disorder (MDD) and OCD produce antibodies for dynorphin. In a study of 105 subjects, OCD and MDD (clinically and biologically related disorders) showed greater reactivity for prodynorphin 209–240 than healthy volunteers, schizophrenics, Alzheimer's disease, multiple sclerosis, and AIDS patients as illustrated in FIG. 1. The absence of reactivity in AIDS and MS illustrates that the antibodies are not a nonspecific consequence of inflammation or infection. The absence of antibodies in schizophrenia and Alzheimer's disease suggests that the antibodies are not nonspecifically related to OCD and MDD. Comparison with age-matched volunteers is shown in FIG. 2.

Antidynorphin antibodies have an unknown origin. However, since some bacteria, plants, and parasites produce peptides with opiate-like immunoreactivity, the antibodies may occur in response to opioid-like epitopes of microbial proteins. If this were true then antidynorphin antibodies might cross-react on synthetic opioid-like sequences from microbial proteins.

Replication B protein 275–290 from *Staphylococcus aureus* plasmids (REPB) has homology with the amino acid sequence for dynorphin A 1–16 (Table 1).

TABLE 1

Homology Between Dynorphin A and Bacterial Replication Protein B 275–290

| Peptide | Amino Acid Sequence |
| --- | --- |
| Dynorphin A 1–16 (SEQ ID NO:2) | Tyr—Gly—Gly—Phe—Leu—Arg—Arg—Ile—Arg—Pro—Lys—Leu—Lys—Trp—Asp—Asn |
|  | \|  \|  \|  :  \|  :  \|  :  \|  \|  :  \|  : |
| REPB 275–290 (SEQ ID NO:3) | Tyr—Gly—Gly—Leu—Leu—Lys—Glu—Ile—His—Lys—Lys—Leu—Asn—Leu—Asp—Asp |

Identical residues are represented by (|) and analogous residues are represented by (:). The sequence REPB 275–290 is identical across *Staphylococcus aureus, Lactobacillus plantarum* and *Bacillus subtilis*, has 81 percent similarity and 50 percent identity with Dyn A 1–16. The greater similarity is for the enkephalin moiety, Tyr—Gly—Gly—Phe—Leu. (SEQ ID NO: 4).

The greater similarity is between the leucine-enkephalin moiety of dynorphin A (Tyr-Gly-Gly-Phe-Leu) (SEQ ID NO: 4) and REPB 275–279 (SEQ ID NO: 5) (Tyr-Gly-Gly-Leu-Leu$^5$). REPB epitopes that are identical to *S. aureus* REPB 275–290 are present on *Lactobacilli plantarum* and *Bacillus subtilis*.

Bacterial plasmids are extrachromosomal DNA that determine important proteins. REP proteins are products of related plasmids present in Staphylococcus, Bacillus, Lactobacilli, Streptococci, Streptomyces, and Clostridia species. These organisms cause common infections and colonize anatomic sites (conjunctiva, skin, oral cavity) with intense sensory innervation. This allows access to sensory ganglia which have no blood brain barrier and direct projections to areas of the central nervous system that have high concentrations of dynorphin.

Streptococcus mutants and Lactobacilli colonize the oral cavity and cooperate to cause dental caries. Streptococcus mutants erodes enamel and promotes secondary invasion of dentine by Lactobacilli. Dental caries are highly prevalent infections and afford access to the central nervous system along the trigeminal nerves. As part of the normal oral flora these organisms may place susceptible humans at risk to the development of antibodies for dynorphin as a consequence of molecular mimicry.

A second set of proteins with homology to dynorphin A derive from a search for proteins with similarity to Arg-Lys-Leu-Lys, (SEQ ID NO: 1), a sequence that has similarity to dynorphin Arg-Pro-Lys-Leu-Lys$^{13}$ (SEQ ID NO: 6), after introduction of a gap for maximum alignment. Arg-Lys-Leu-Lys (SEQ ID NO: 1) is a widely distributed epitope, present on both environmental and human proteins (Table 2).

TABLE 2

Proteins that Display Arg—Lys—Leu—Lys

| Peptide Sequence | Amino Acid |
| --- | --- |
| Microorganisms: | |
| *Streptococcus pyogenes* 6M −27 to −30 (SEQ ID NO: 1) | Arg—Lys—Leu—Lys. |
| *Staphylococcus aureus* exfoliative toxin B 40—43 (SEQ ID NO: 1) | Arg—Lys—Leu—Lys |
| *Plasmodium falciparum* calmodulin 241–244 (SEQ ID NO: 1) | Arg—Lys—Leu—Lys |
| Influenza B hemagglutinin 2 481–484 (SEQ ID NO: 1) | Arg—Lys—Leu—Lys |
| E. coli phosphoenolpyruvate carboxylase 109–112 (SEQ ID NO: 1) | Arg—Lys—Leu—Lys |
| *Saccharomyces cerevisiae* (Baker's yeast) | Arg—Lys—Leu—Lys |

TABLE 2-continued

Proteins that Display Arg—Lys—Leu—Lys

| Peptide Sequence | Amino Acid |
| --- | --- |
| fatty acid synthase 412–415 (SEQ ID NO: 1) | |
| Human Proteins: | |
| GABA receptor (SEQ ID NO: 7) | Arg—Lys—Ala—Lys |
| Glutamate decarboxylase 308–311 (SEQ ID NO: 1) | Arg—Lys—Leu—Lys |
| Rabbit calsequestrin 259–262 (SEQ ID NO: 1) | Arg—Lys—Leu—Lys |
| Ca$^{++}$/calmodulin-dependent protein kinase 298–301 (SEQ ID NO: 1) | Arg—Lys—Leu—Lys |
| Ryanodine (calcium-channel) receptor 4059–4062 (SEQ ID NO: 8) | Leu—Lys—Leu—Lys |
| Human DNA polymerase 1431–1434 (SEQ ID NO: 1) | Arg—Lys—Leu—Lys |
| Gibbon IL-3 128–131 (SEQ ID NO: 1) | Arg—Lys—Leu—Lys |
| Diffuse B cell lymphoma proto-oncogene 169–172 (SEQ ID NO: 1) | Arg—Lys—Leu—Lys |

In particular it is present on several *Streptococcus pyogenes* and S. mutants proteins, Influenza B virus hemagglutinin, 472–475, and *Plasmodium falciparum* calmodulin. These organisms are associated with post-infectious neuropsychiatric disorders and autoimmune phenomena secondary to molecular mimicry. *Staphylococcus aureus* exfoliative toxin B (impetigo), *Saccharomyces cerevisiae* (Baker's yeast), *Bacillus subtilis, Escherichia coli*, and Epstein-Barr virus (infectious mononucleosis) proteins also display Arg-Lys-Leu-Lys (SEQ ID NO: 1).

These organisms are common causes of disease, and in the case of Baker's yeast and *B. subtilis*, are employed extensively in the manufacture of foods. Thus, there is ample exposure for sensitization to Arg-Lys-Leu-Lys (SEQ ID NO: 1) in genetically susceptible or immunocompromised individuals. Cross-reactivity does not ensure autoimmunity. The immunogenicity of the sequence is not clear but is inferred by its homology to highly immunogenic Streptococcal epitopes Ile-Arg-Leu-Arg (SEQ ID NO: 9), the cause of autoimmunity for renal glomeruli, and Gln-Lys-Ser-Lys (SEQ ID NO: 10), one target of autoimmunity for cardiac myosin.

SUMMARY OF THE INVENTION

This invention provides a method for detecting, in human body fluid, the presence of antibodies for *Staphylococcus aureus* REPB 275–290 and Arg-Lys-Leu-Lys (SEQ ID NO:

1), bacterial, protozoal, or viral peptides that resemble dynorphin A 1–16. This invention, also, provides a method for correlating psychobiological disorders in humans with microbial epitopes as reflected by a blood level of antibodies having specificity for dynorphin A, *Staphylococcus aureus* REPB 275–290, or Arg-Lys-Leu-Lys (SEQ ID NO: 1).

The reactivity of human dynorphin antisera for synthetic microbial peptides, that are homologous to differing sequences of dynorphin A, might relate to the cause of anti-dynorphin antibodies and point to functional consequences.

DETAILED DESCRIPTION OF THE INVENTION

Figure 1:
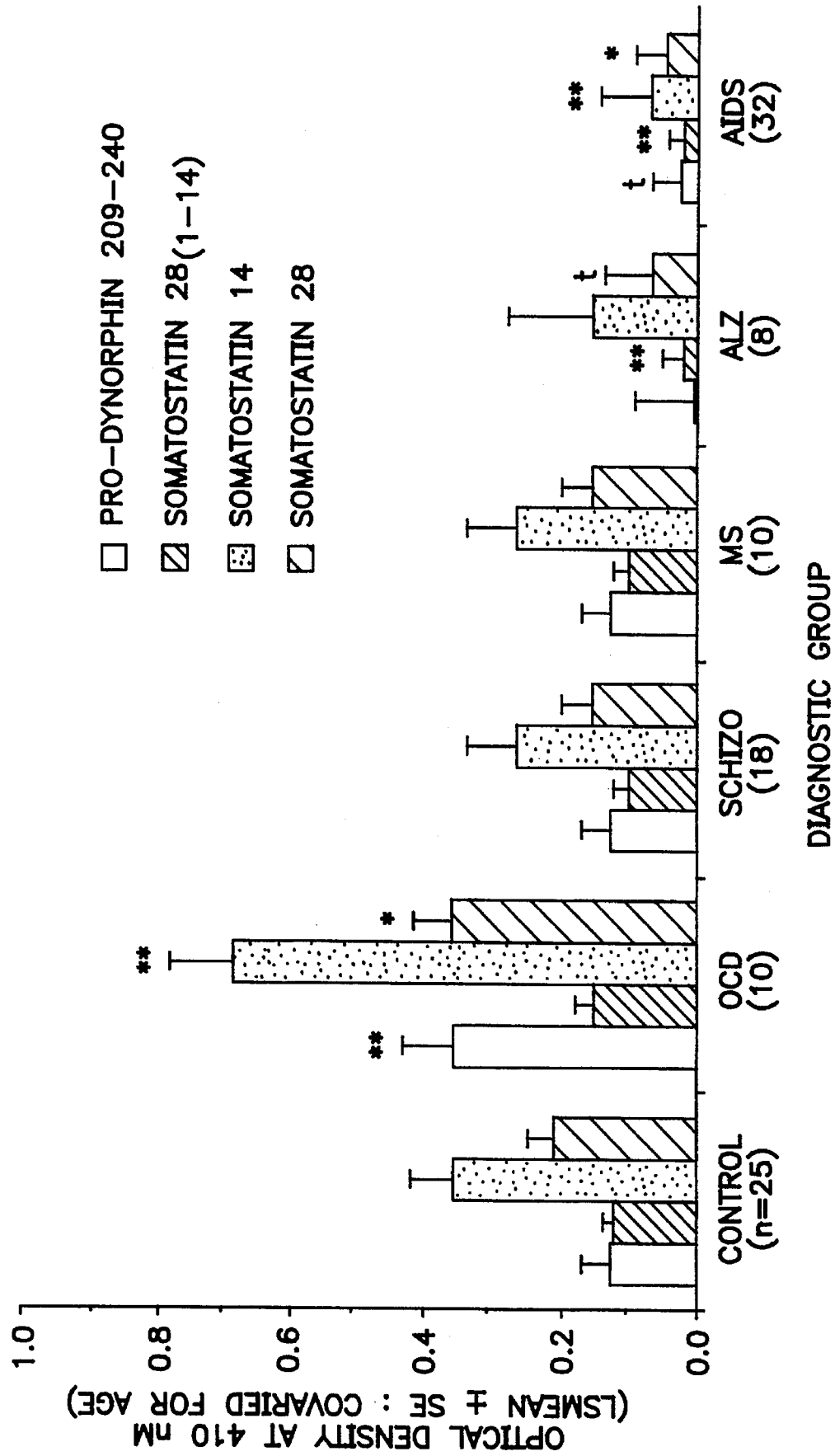
FIG. 1 is a graph of patient reactivity for prodynorphin 209–240 between groups of patients.
Figure 2A:
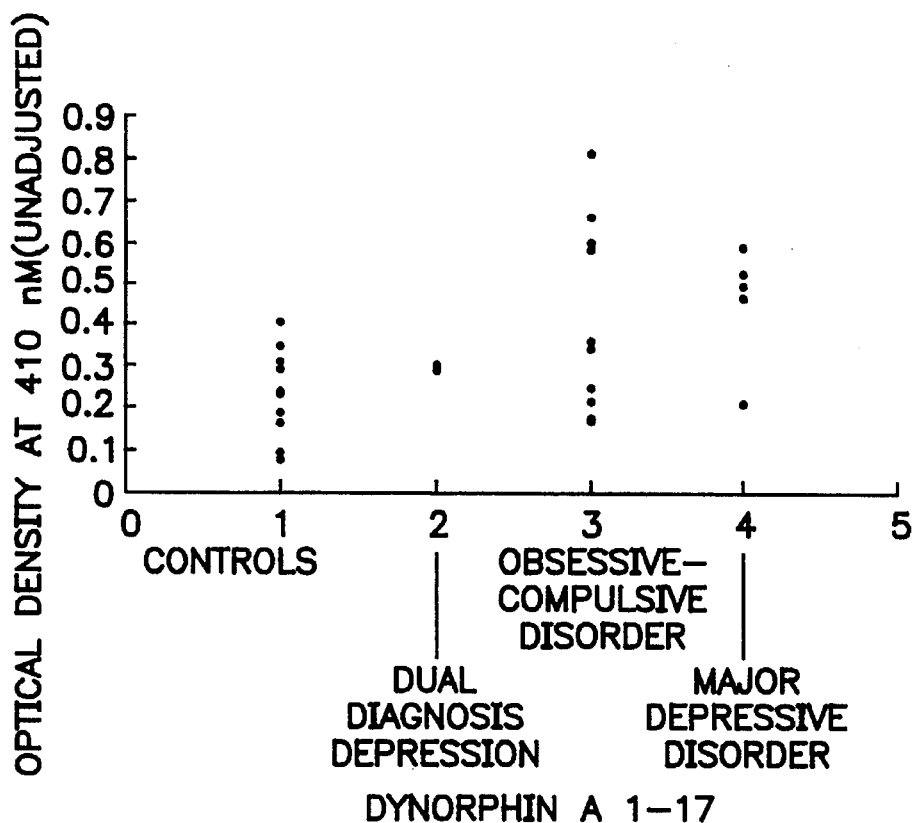
FIG. 2 is four graphs comparing reactivity in age-matched groups of patients. SEQ ID NO: 1 is also shown in this Figure.
Figure 2B:
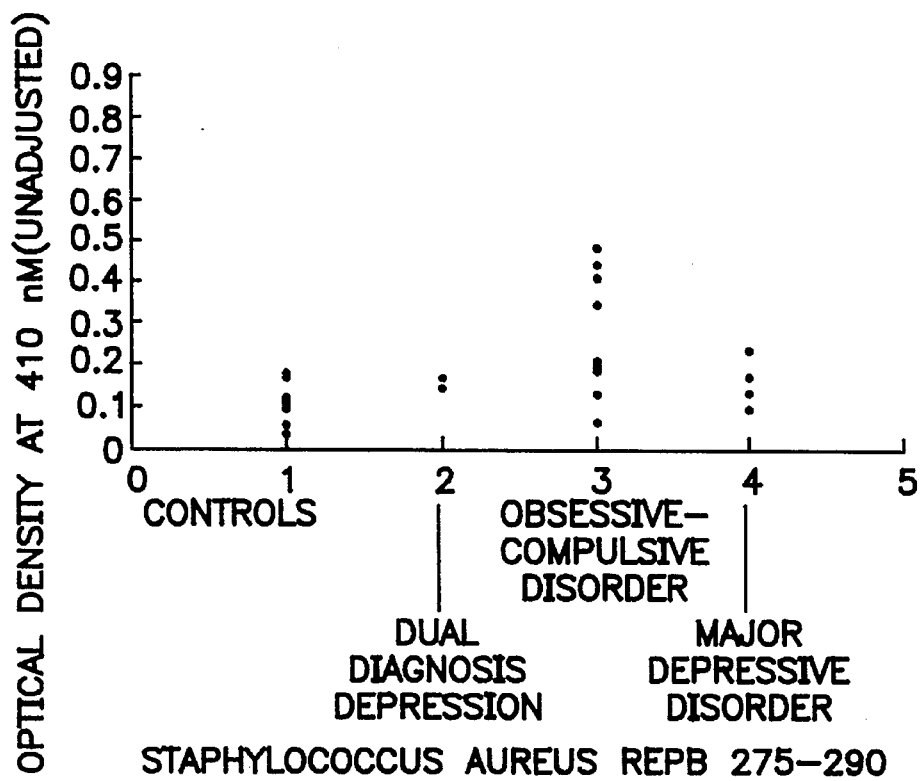
Figure 2C:
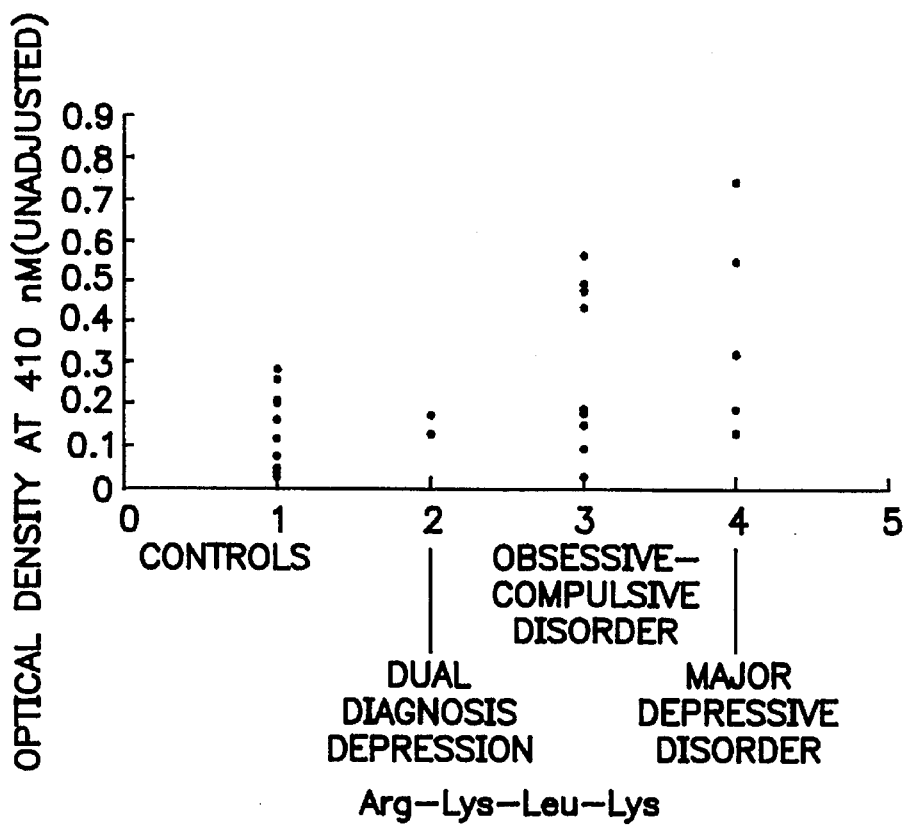
Figure 2D:
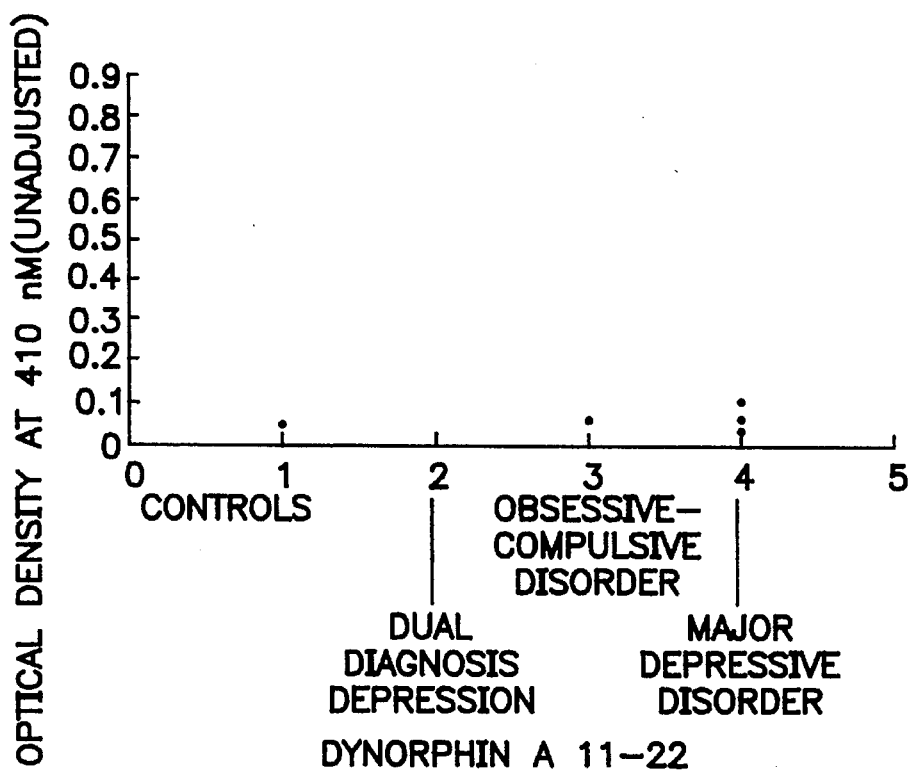

The invention is a method for detecting in a sample of human body fluid the presence of specific antibodies against *Staphylococcus aureus* REPB 275–290 and Arg-Lys-Leu-Lys (SEQ ID NO: 1), microbial peptides that mimics the brain peptide Dynorphin A 1–16 comprising the following steps:

(a) coating a multiwell plate with a solution of microbial peptide with similarity to neuropeptide to be detected, sealing the plate with an adhesive cover, incubating the plate for more than 24 hours with the solution at about 0° to 4° C. with a blocking step;

(b) allowing a sample of human body fluid containing immunoglobulin in which the presence of antibody to the neuropeptide and homologous microbial peptide is to be detected, to react with the coated plate (sealed with an adhesive cover) in humidified air containing about 5 to 7 percent $CO_2$ for about 1.5 to 3 hours at about 37° C.;

(c) washing the plate with a buffered detergent more than 5 times to remove unbound material from the plate;

(d) allowing anti-human antibody conjugated with a marker entity to react for about 1.5 to 3 hours (after sealing the plate with an adhesive cover) in humidified air containing about 5–7 percent $CO_2$ for about 1.5 to 3 hours at about 37° C. with the washed plate of step (c) to allow binding conjugated-antibody with the human antibody bound to the neuropeptide;

(e) removing the unreacted material from the plate by washing more than 5 times as in step (c);

(f) determining the presence of the marker by enzymatic, spectrophotometric, immunologic, fluorescentphotometric, or radioisotopic assay and comparing with a control sample treated identically as in step (a) through step (e), a reading above the control being indicative of the presence of antibody against the neuropeptide or the homologous environmental protein.

The preferred methods and materials for invention are described below. The term opioid peptide includes such entities as β-endorphin, leucine enkephalin, dynorphin, methionine enkephalin, and the like.

PREFERRED MATERIALS AND METHODS

Subjects

Asymptomatic volunteers (N=10) and patients classified as major depressive disorder (MDD; N=6) or obsessive-compulsive disorder (OCD; N=10) by criteria of the American Psychiatric Association (Diagnostic Statistical Manual for Mental Disorders, Third Edition—Revised, 1987 DSM-III-R;58) provided serum for testing. Three additional patients with MDD had a concurrent dual diagnosis; 1 confirmed narcolepsy, 1 combat-related post-traumatic stress disorder, and 1 panic disorder.

Identification of Bacterial Proteins with Homology to Dynorphin A

A computer-assisted Pearson and Lipman search of the National Biomedical Research Foundation database identified bacterial and plasmid peptides with homology to dynorphin A 1–17. Replication B protein 275–290 from *Staphylococcus aureus* plasmids has homology with the amino acid sequence for dynorphin A 1–16. (Table 3).

TABLE 3

| Diagnosis | Prodynorphin 209–240 | Dynorphin A 1–17 | REPB 275–290 | Arg—Lys—Leu—Lys | Dynorphin A 11–22 |
|---|---|---|---|---|---|
| Controls | 0.449 ± 0.088 | 0.229 ± 0.034 | 0.088 ± 0.012 | 0.133 ± 0.030 | 0.009 ± .005 |
| OCD | 0.894 ± 0.129 | 0.412 ± 0.074 | 0.259 ± 0.045 | 0.259 ± 0.058 | 0.011 ± .006 |
| MDD | 1.508 ± 0.164 | 0.511 ± 0.081 | 0.142 ± 0.021 | 0.358 ± 0.087 | 0.053 ± .015 |
| Dual Dx MDD* | 0.929 ± 0.097 | 0.292 ± 0.007 | 0.186 ± 0.009 | 0.160 ± 0.014 | 0.001 ± .001 |
| OCD | t = 2.86, p < .013 | t = 2.12, p < .048 | t = 3.90, p < .001 | NS | NS |
| MDD | t = 6.26, p < .001 | t = 3.73, p < .009 | t = 2.20, p < .045 | t = 2.60, p < .021 | NS |
| Dual Dx MDD* | t = 3.42, p < .003 | t = 1.89, p < .077 | t = 4.82, p < .000 | NS | NS |

*Because of the small N = 3, compared metric data for individual wells (N = 9) rather than the means of triplicates against the means of triplicates for healthy volunteers.

The greater similarity is for the leucine-enkephalin moiety (Tyr-Gly-Gly-Phe-Leu) (SEQ ID NO: 4) of dynorphin A. A second set of proteins derived from a search for proteins with similarity to Arg-Lys-Leu-Lys (SEQ ID NO: 1), a sequence that has similarity to dynorphin Arg-Pro-Lys-Leu-Lys[13] (SEQ ID NO: 6) after introduction of a gap for maximum alignment. This protein is present in *Streptococcus pyogenes* 6M -27 to -30, Influenza B virus hemagglutinin, 472–475, and *Plasmodium falciparum* calmodulin.

Enzyme Linked Immunoadsorbent Assay (ELISA)

Serum samples and later dilutions were centrifuged at 17,000×g for 15 minutes before application to the plates. Sera were diluted to approximately equal IgG concentrations as determined by radial immunodiffusion (Kallestad Laboratories, Inc., Austin, Tex.). The IgG concentrations of the final dilutions of serum were determined before assay in triplicate after random assignment to microliter plates.

Dynorphin A 1–17, *Staphylococcus aureus* plasmid pUB110 replication protein B 275–290 (REPB), Arg-Lys-Leu-Lys (SEQ ID NO: 1), and Dynorphin A 11–22 were prepared at a standard concentration of 10 µg/mL in pH 9.4 coating buffer and pipetted in a 100 µl volume into separate wells of an Immulon I polystyrene plate (Dynatech, Arlington, Va.) and allowed to stand at 0° C. overnight. The plate was washed with 0.5% Tween 20 (Fisher) in phosphate-buffered saline (PBS; pH 7.3, without calcium or magnesium). Then 100 µl of a 1% solution of bovine plasma albumin in PBS, was added for 1 hour to block unbound sites on the plastic and reduce nonspecific binding of human antibody. The plate was washed again with 0.5% Tween 20 in PBS. Then human serum samples in 100 µl volumes were added and allowed to bind for 2 hours at 37° C. The plate was then washed, and 100 µl of a 1:200 dilution of an alkaline phosphatase-conjugated goat anti-human IgG (heavy chain specific) antibody (Sigma Chemical Co., St. Louis, Mo.) was pipetted into each well. After 2 hours at 37° C., the plate was washed, 100 µl of the alkaline phosphatase substrate p-nitrophenyl phosphate (disodium salt) dissolved in 10% ethanolamine was added to each well, and the reaction was allowed to proceed at 37° C. in the dark. Substrate catalysis was determined by optical density (OD) units read on an automatic micro-ELISA spectrophotometer (Dynatech Instruments, Torrence, Calif.). Values represent the means ± SD of triplicate OD readings at 410 nM. The background binding of secondary goat antibodies to peptide served as negative controls. Binding to peptides was compared at equal reaction times.

Using this method, mean optical density measurements ± standard error (S.E.) were determined for comparison groups. Student's t-test was performed for each variable after logarithmic transformation of metric data of unadjusted means. Patient groups were compared to healthy controls.

Binding to [$^3$H]Dynorphin A 1–8

Dilutions of MDD, OCD, and normal sera were centrifuged at 17,000×g. Then duplicate 100 µl aliquots were incubated with 100 µl of [$^3$H]dynorphin 1–8 (New England Nuclear Products, Boston, Mass.) overnight. Free radiolabelled ligand was adsorbed to charcoal. After centrifugation bound tritiated ligand was counted in supernatants using liquid scintillation in a Beckman LS 9800 (Beckman Instruments, Inc., Irvine, Calif.). Total disintegrations per minute (DPM) were averaged and net DPM calculated by subtraction of background from each sample. The net DPM were then normalized by dividing by the IgG concentrations.

Figure 3:
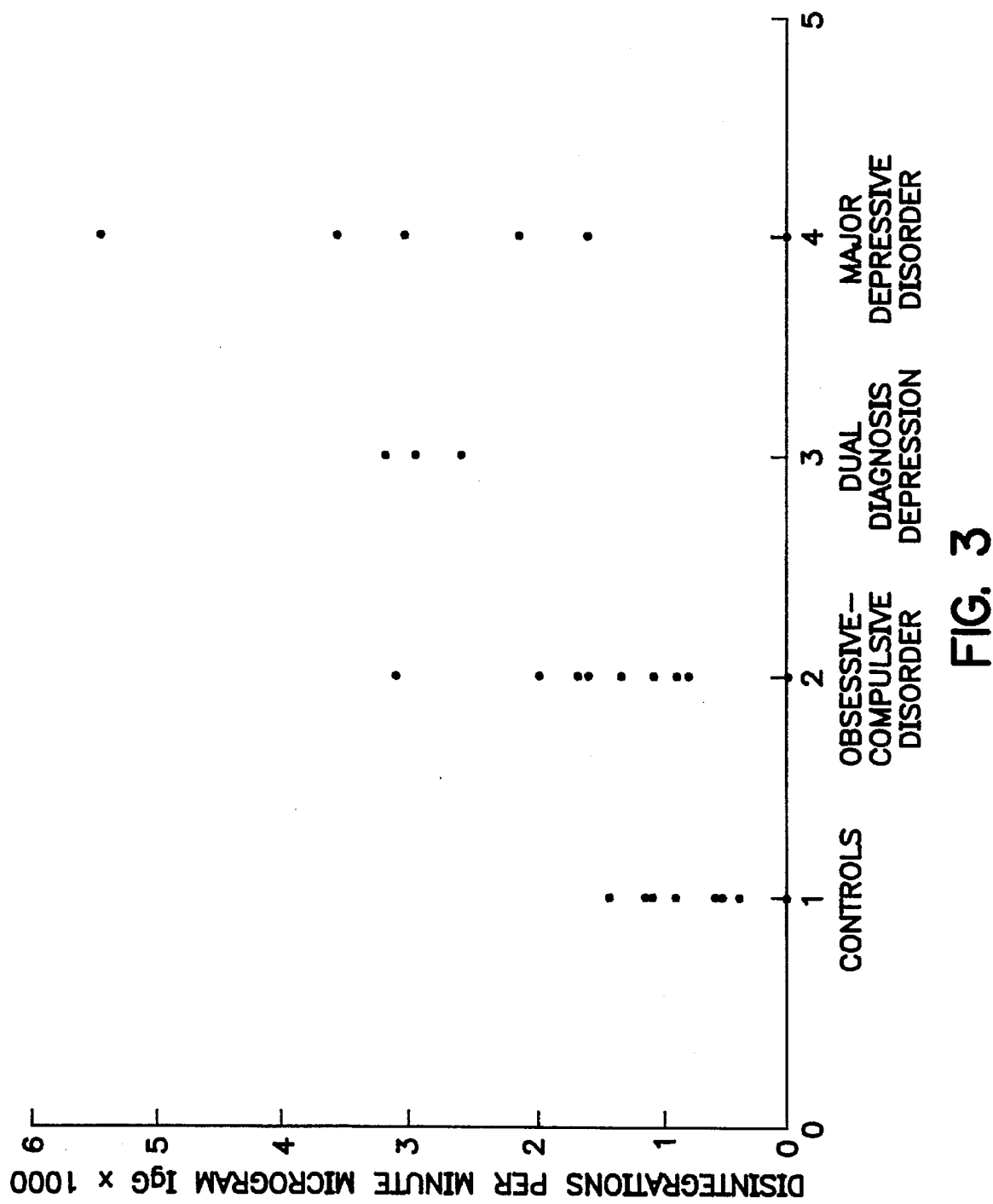
FIG. 3 is a graph comparing binding of normal sera with MDD and OCD sera.

Serum antibody bound [$^3$H]Dynorphin A 1–8. MDD and OCD sera showed significantly greater binding to radiolabelled dynorphin (2633±757 DPM/µg IgG; t=3.24, p<0.006, and, 1385±289; t=2.26, df=17, p<0.037, respectively) than normal sera (669±152 DPM/µg IgG). (FIG. 3) The bacterial peptides absorb out antibodies for dynorphin. Several subjects had as much as an 80% reduction in binding to [$^3$H]Dynorphin A 1–8 after adsorption of sera with *S. aureus* REPB, but the differences for groups were not significant.

Figure 4A:
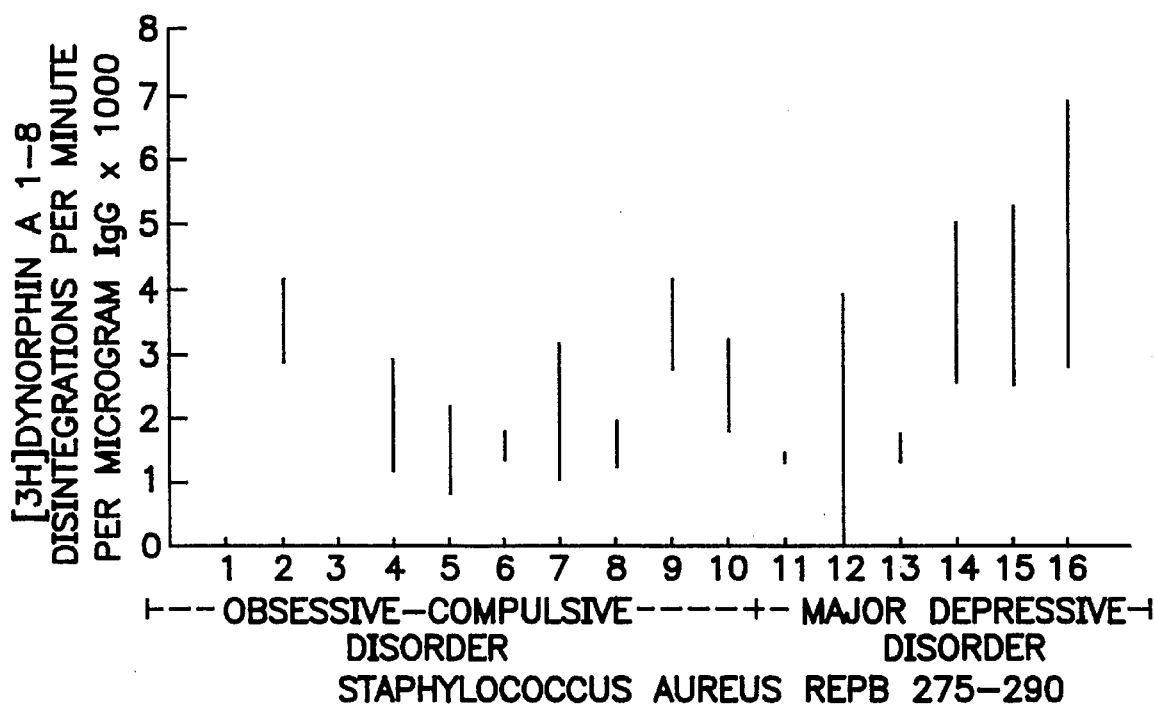
FIG. 4 is a graph of the percent change of binding for *S. aureus* REPB.
Figure 4B:
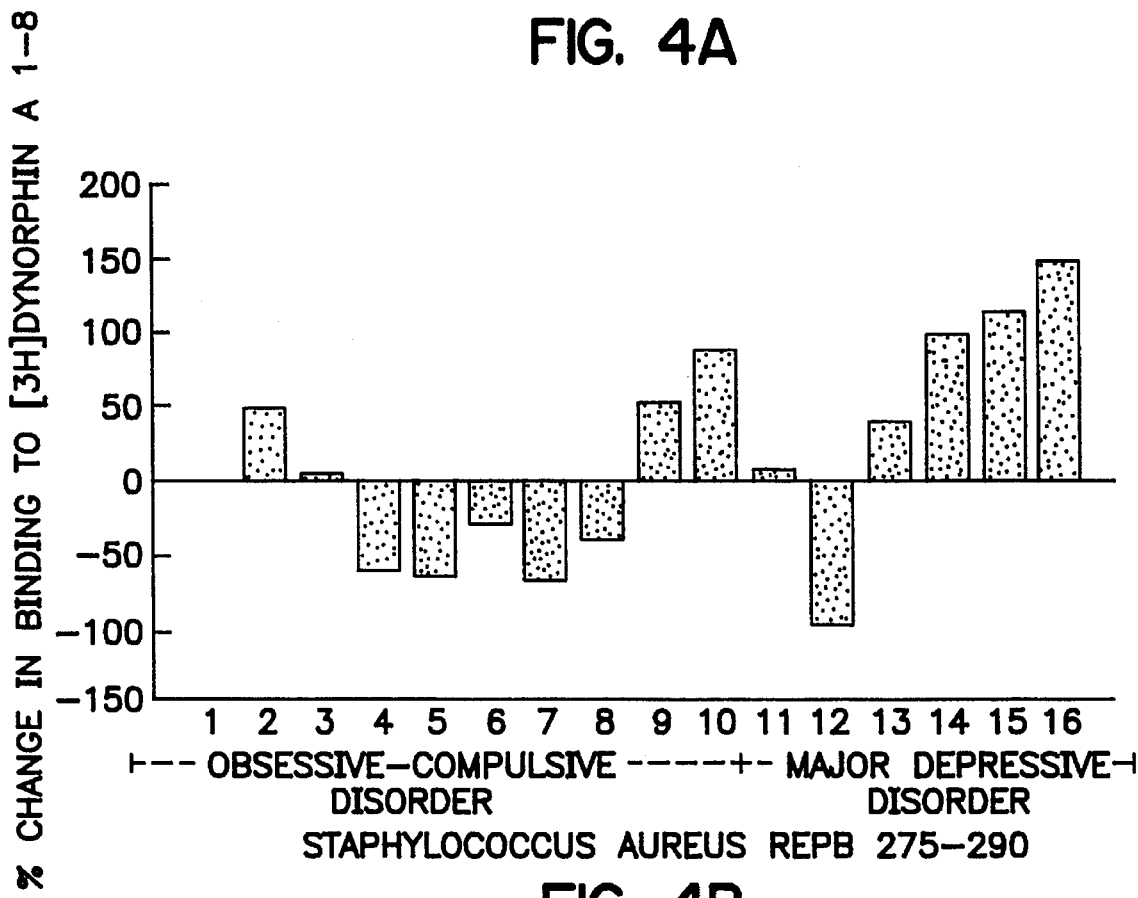
Figure 5B:
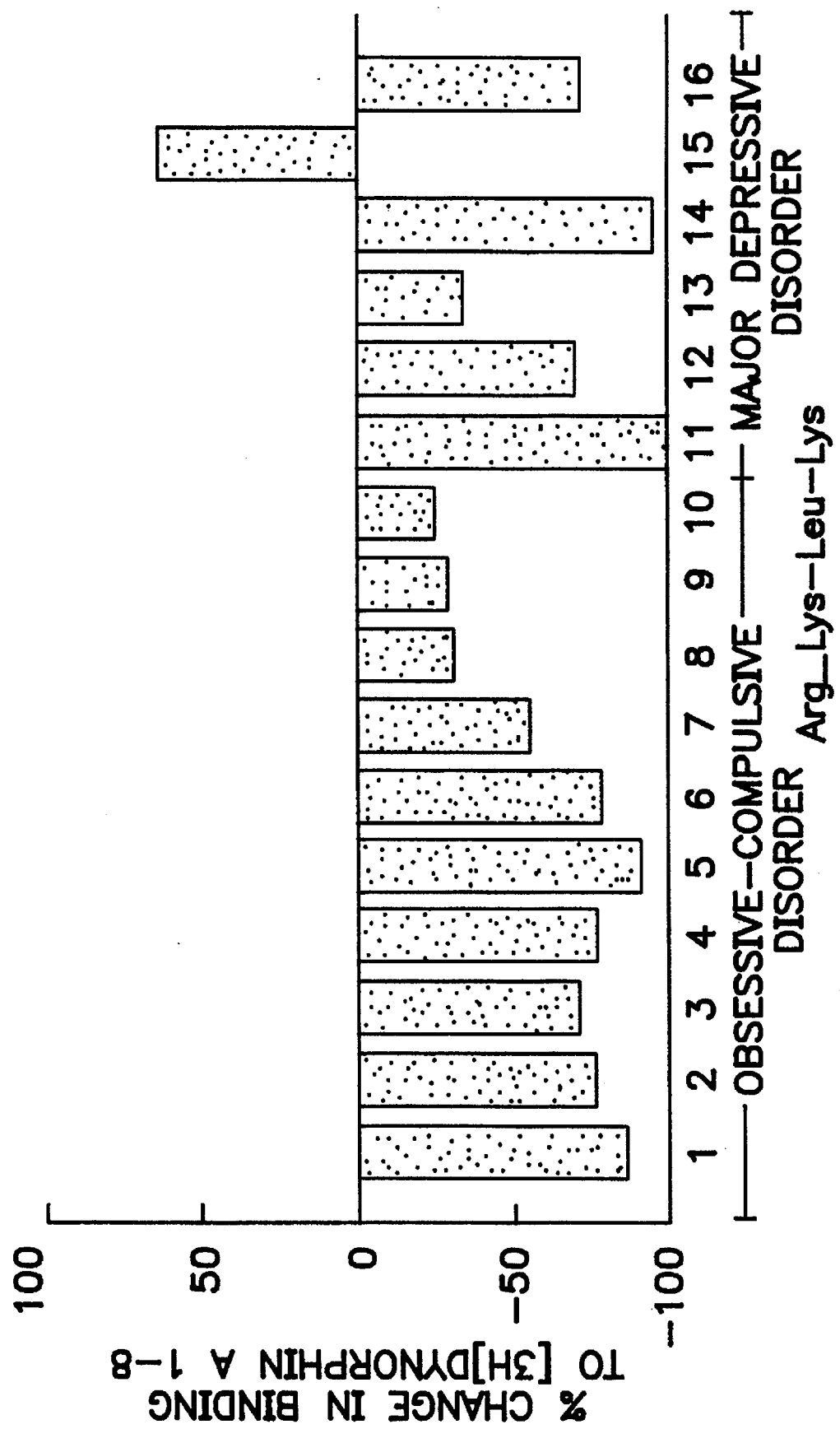
FIG. 5 is a graph of the percent change of binding for Arg-Lys-Leu-Lys (SEQ ID NO: 1).

(FIG. 4) Adsorption of dynorphin antisera with $10^{-7}$M Arg-Lys-Leu-Lys (SEQ ID NO: 1) inhibited binding to [$^3$H]Dynorphin A 1–8 by 41% (paired t=5.19, df=15, p<0.0001). These preliminary data suggest that polyclonal sera may comprise antibodies that recognize fragments of dynorphin A 1–17 as small as Tyr-Gly-Gly-Phe-Leu[5] (SEQ ID NO: 4) or Arg-Pro-Lys-Leu-Lys (SEQ ID NO: 6), and others that bind to larger segments of the dynorphin molecule. (FIG. 5).

Affinity Chromatography

To further assess the activity of anti-dynorphin antibodies, the antibodies were isolated using affinity chromatography. Immunoglobulin G was purified from cerebrospinal fluid using protein A (*Staphylococcus aureus*). Purified IgG samples were adsorbed to synthetic human dynorphin A 1–17 coupled to cyanogen bromide activated Sepharose 4B (Pharmacia, Upsaala, Sweden). Elution was performed using 3M potassium thiocyanate and 4M guanidine hydrochloride.

Antibodies for dynorphin were purified from the cerebrospinal fluid (CSF) of a patient with human immunodeficiency virus type 1-positive a 20 year history of heroin abuse and major depression, and a one year history of advanced human immunodeficiency virus (HIV-1) infection (Table 4).

TABLE 4

| CSF ANTI-DYNORPHIN ANTIBODY BINDING TO NEUROPEPTIDES | |
|---|---|
| Prodynorphin 209–240 | 0.585 ± 0.08 |
| β-Endorphin | 0.450 ± 0.03 |
| Dynorphin A 1–17 | 0.152 ± 0.021 |
| β-Neo-endorphin | 0.103 ± 0.018 |
| Dynorphin A 2–17 | 0.053 ± 0.004 |
| Tumor Necrosis Factor | 0.051 ± 0.003 |
| Cholecystokinin | 0.043 ± 0.008 |
| Preproenkephalin B 186–204 | 0.034 ± 0.002 |
| β-Lipotropin 88–91 | 0.032 ± 0.001 |
| Methionine Enkephalin | 0.030 ± 0.004 |
| Preproenkephalin B 226–254 | 0.028 ± 0.005 |
| -Neo-endorphin | 0.022 ± 0.003 |
| Substance P | 0.018 ± 0.002 |
| Corticotropin | 0.016 ± 0.004 |
| -Melanotropin | 0.009 ± 0.002 |
| Angiotensin II | 0 |
| Vasoactive Intestinal Peptide | 0.009 ± 0.004 |
| 2.5S Nerve Growth Factor | 0.030 ± 0.007 |

The use of unclean syringes leads to frequent Staphylococcal bacteremias and skin abscesses in heroin abuse. Routine CSF studies were normal. However, binding to prodynorphin 209–240, as measured by optical density (OD) in an ELISA ($OD_{410}$=0.890±0.110), exceeded levels for 21 neurological disease control CSF samples ($OD_{410}$=0.160±0.035; t=6.18, df=21, p<0.0001). This binding was an unlikely effect of CNS infection or inflammation since patients with viral encephalitis and multiple sclerosis, included among the controls, showed negligible binding. Binding to β-endorphin was 77% the OD for prodynorphin. However, binding to des-Tyr-dynorphin A 2–17, a non-opioid peptide, was negligible. REPB and dynorphin A 1–17 mutually inhibited affinity purified CSF anti-dynorphin antibody binding to either peptide (Table 5).

TABLE 5

Affinity Purified CSF Anti-Dynorphin IgG Binds Bacterial Replication Protein B[a] 275–290

| Peptide | Amino Acid Sequence | Optical Density at 410 nM After Adsorption by: PBS | Dynorphin A | REPB | Binding to $[^3H]$Dynorphin A 1–8 DPM/μg IgG[b] |
|---|---|---|---|---|---|
| PBS | | | | | 11,585 ± 915 |
| Dynorphin (SEQ ID NO:2) | Y G G F L R R I R P K L K W D N | 0.483 ± 0.074 | 0.110 ± 0.055* | 0.005 ± 0.004** | 4,315 ± 870†† |
| | ¦ ¦ ¦ : ¦ : ¦ : ¦ ¦ : ¦ : | | | | |
| REPB (SEQ ID NO:3) | Y G G L L K E I H K K L N L D D | 0.307 ± 0.037 | 0.084 ± 0.052* | 0.052 ± 0.033** | 5,450 ± 975† |

[a] A Pearson and Lipman search of the National Biomedical Research Foundation protein sequence database for sequences with similarity to dynorphin A 1–17 identified replication protein B 275–290 (REPB) from *Staphylococcus aureus*, *Lactobacillus plantarum* and *Bacillus subtilis* plasmids. The letter key for amino acids is: D = aspartate, E = glutamate, F = phenylalanine, G = glycine, H = histidine, I = isoleucine, K = lysine, L = leucine, N = asparagine, P = proline, R = arginine, W = tryptophan, and Y = tyrosine. Identical residues = (¦); analogous residues = (:). The concentration of peptides is 10 μg/ml, while the concentration of IgG was 200 ng/ml. Means for triplicate measures of binding to dynorphin and REPB were significantly greater than 3 control CSF samples ($t = 6.11$, $df = 9$, $p < .001$, and, $t = 2.79$, $df = 9$, $p < .021$, respectively). There was negligible binding to tumor necrosis factor, corticotropin, nerve growth factor, substance P, vasoactive intestinal peptide, α-melanotropin, preproenkephalin B 186–204, cholecystokinin, angiotensin II, and several other non-opiate fragments of dynorphin. Antibody was adsorbed with $10^{-7}$ M dynorphin A 1–17 or REPB 275–290. Significance of inhibition: * = $p < .025$; ** = $p < .01$.
[b] DPM = disintegrations per minute/μg IgG of $[^3H]$Dynorphin A 1–8. Significance of inhibition: ††: $t = 153.0$, $df = 1$, $p < .004$; †: $t = 10.96$, $df = 1$, one-tailed $p < .029$. Four control CSF bound 501 ± 9 DPM/μg IgG ($t = 9.82$, $p < .003$), while 10 normal sera bound 669 ± 152 DPM/μg IgG. PBS = phosphate buffered saline.

HIV-1 does not display opiate-like sequences. Furthermore, non-drug abusing HIV-positive subjects had negligible serum reactivity for prodynorphin 209–240, dynorphin A 1–17 or REPB 275–290. Therefore it is most likely this patient's antibodies for both dynorphin and REPB are related to heroin abuse. There is the chance that REPB induced antibodies for dynorphin.

These preliminary data lead to the conclusion that similarity in protein structure can lead to cross-reactive immunity for dynorphin. The binding of antidynorphin antibodies to REPB is consistent with studies of experimentally induced antibodies. Monoclonal antibodies for dynorphin A leucine-enkephalin, Tyr-Gly-Gly-Phe-Leu[5] (SEQ ID NO: 4), show high affinity binding to a number of homologous, but non-identical peptides, particularly Tyr-Gly-Gly-Leu-Leu (SEQ ID NO: 5) which comprises REPB 275–278.

There are no prior examples of molecular mimicry in primary psychiatric disorders. However, the occurrence of psychiatric sequelae with epitope-specific immunity indirectly supports the potential meaningfulness of immunity for dynorphin, REPB, and Arg-Lys-Leu-Lys (SEQ ID NO: 1) to psychiatric disorders. Systemic lupus erythematosus (SLE) is an autoimmune disease with prevalent psychiatric sequelae, making SLE a strong model for immune mechanisms in psychiatric disease. A connection between molecular mimicry and psychiatric symptoms occurs with SLE. The etiology of SLE may be due to molecular mimicry. Early studies proposed that the psychotic symptoms of SLE were related to autoimmunity for neurons. Antineuronal antibodies in cerebrospinal fluid correlated with psychosis and damage to the blood-brain barrier as a result of immune complex deposition in the choroid plexus. However, more recent work has linked SLE psychosis to antibodies for specific epitopes of ribosomal P protein. These antibodies are predictive of SLE psychosis and target an epitope 22 amino acids in length. This epitope has no homology with dynorphin, REPB, or Arg-Lys-Leu-Lys (SEQ ID NO: 1). Thus, SLE illustrates the potential association between epitope-specific immunity and alterations in behavior. However, no prior connections have been made between primary psychiatric disorders, microbial peptides, molecular mimicry of a neuropeptide, and immunity for the neuropeptide.

Therefore, these data are consistent with existing studies and potentially connect environmental antigens and immunity for dynorphin to behavioral disorders. The potential clinical utility of the test is presently indicated by anecdotal and epidemiological evidence that link epitope-specific immunity for dynorphin, REPB, and Arg-Lys-Leu-Lys (SEQ ID NO: 1) to psychiatric disorders. This use includes the association between diagnostic categories and infectious agents, as well as the case histories of patients who demonstrate antibodies.

Replication Protein B 275–290

Patients with OCD and dual diagnosis MDD showed the greatest reactivity for REPB 275–290. However, there is no established connection between organisms that display REPB 275–290 and OCD. Despite this, reduced levels of serum β-endorphin reported in OCD support the possibility of autoimmunity for dynorphin.

Of the patients with dual diagnosis MDD, a Vietnam veteran with combat-related post-traumatic stress disorder (PTSD) exhibited antibodies for REPB 275–290. Because of the exposure of Vietnam combatants to micro-organisms that produce opioid-like peptides, cross-reactive immunity for opioid peptides and homologous microbial peptides might relate to the pathogenesis of PTSD. The serum from the Vietnam veteran with PTSD and a history of pyoderma showed binding to the *S. aureus* sequence, but negligible reactivity for dynorphin A 11–22 (Table 6). Adsorption of serum with REPB inhibited antibody binding to $[^3H]$Dynorphin A 1–8.

TABLE 6

Anti-Dynorphin From PTSD Binds Homologous Microbial Peptides

| Peptide | Amino Acid Sequence | Optical Density at 410 nM Normals (N-10) | Patient | % of Inhibition Binding to [³]Dynorphin A 1–8 |
|---|---|---|---|---|
| Dynorphin (SEQ ID NO:2) | Y G G F L R R I R P K L K W D N | 0.109 ± 0.029 | 0.380 | 70% |
| REPB (SEQ ID NO:3) | Y G G L L K E I H K K L N L D D | 0.042 ± 0.014 | 0.242 | 30% |
| S. PYOGENES 6M (SEQ ID NO:1) | R – K L K | 0.069 ± 0.023 | 0.180 | 28% |

Bind to [³]Dynorphin A 1–8 for the patient was 2,593 disintegrations per minute per μg of IgG while that for normal serum was 669 ± 152 DPM per μg of IgG.

PTSD is a disorder where the majority of subjects and controls have had identifiable exposure to *S. aureus*. PTSD is best studied in veterans of the Vietnam War. However, World War II veterans of the South Pacific theater also have a higher incidence of PTSD than veterans of the European theater, despite experiencing similar combat intensity.

An association between PTSD and Staphylococcal skin infections acquired in Vietnam or the South Pacific is apparent in a preliminary study of the incidence of pyoderma in PTSD. In Vietnam "jungle rot" was a fungal skin infection caused by a zoophilic variety of *Trichophyton mentagrophytes*. Exposure to the fungus in soil and poor skin hygiene in humid climate favored chronic infection. In contrast to its causation of benign tinea versicolor in the United States, Vietnamese *T. mentagrophytes* was an aggressive organism that caused extensive inflammation. This promoted secondary skin infection by penicillin-resistant *Staphylococcus aureus* and Group A Streptococci. These skin diseases had a 12 percent incidence and accounted for half all surgical and medical disease and up to 80 percent of outpatient visits and lost man-hours in Vietnam.

Similar observations were made during World War II where the incidence of pyoderma was much higher in soldiers who served in the South Pacific compared to soldiers who served in Europe. However, in the South Pacific the primary agent of "jungle rot" was cutaneous *Corynebacterium diphtheria*. However, this infection was also complicated by secondary *Staphylococcus aureus* (65 percent). The European theater suffered a high incidence of nasopharyngeal diphtheria, rheumatic fever, scarlet fever, and strept throat, but not *Staphylococcus aureus* or other skin infection. Thus, *S. aureus* stands out as a distinguishing organism, and skin infection as a portal of entry which could potentially give access to sensory ganglia and thence to the CNS.

An estimated 15 percent of Vietnam veterans suffer current post-traumatic stress disorder. Although the National Vietnam Veterans Readjustment Study understandably emphasized combat and exposure to grotesque death as risk factors for PTSD, combat troops with PTSD were not compared to combat troops without PTSD which might have identified other potential factors for PTSD. No correlations were sought with specific medical illnesses.

Yet, several observations suggest that environmental factors may contribute to the pathogenesis of PTSD. Combat-related PTSD is most severe in veterans once active in tropical climates between the 10th and 20th parallels (Vietnam and the South Pacific). Monozygotic twin pairs with concordance for Vietnam service show a 12 percent incidence of PTSD, while twin pairs discordant for Vietnam service are discordant for PTSD.

An unrecognized relationship between PTSD and cross-reactive immunity can exist. In a survey of 308 outpatient clinic visits 81/99 patients with PTSD reported a history of pyoderma compared to 23/209 subjects without PTSD ($X^2=147.5$ df=1, p<0.00001; Pearson's r=0.70, p<0.00001). The occurrence of pyoderma with PTSD might be an incidental association since PTSD was more common among combatants (89/124) than noncombatants (10/184; $X^2=146.4$ df=1, p<0.00001; Pearson's r=0.70, p<0.00001) while 8/124 of combatants reported pyoderma compared to 16/184 non-combatants ($X^2=125.7$ df=1, p<0.00001; Pearson's r=0.65, p<0.00001). However, the relationship between PTSD and pyoderma persisted despite control for equivalent exposure to combat and infection. Pyoderma affected 78/89 combatants with PTSD (63/72 Vietnam, 4/5 Korean War, 6/6 South Pacific, 2 Panama, 1 Guyana, 2 Vietnam era) compared to 10/35 combatants without PTSD. Using log-linear model analysis, the association between PTSD, pyoderma, combat, and geographic assignment was significant (Pearson's $X^2=1227.7$ and Likelihood ratio $X^2=650$, df=53, p<0.00001). Combatants of the World War II South Pacific theater exhibited a significantly higher association between PTSD and pyoderma (6/10) compared to 0/10 veterans of the European theater ($X^2=34.35$, df=5, p<0.0001). Two of 5 women with PTSD were Vietnam nurses who reported pyoderma, of the remaining three 1 was sexually assaulted, and 2 were abused by their spouses. In contrast, 0/16 women without PTSD reported pyoderma.

These preliminary epidemiological data and the reactivity of a single serum raise consideration that there may be a potential relationship between the causative agents of pyoderma and PTSD, and point to infection as a predictive factor for PTSD. The reactivity for dynorphin and opioid-like peptides is consistent with studies that suggest that reduced plasma β-endorphin and neurophysiological sequelae of PTSD relate to mechanisms that involve alterations in opioid peptides.

Fungi exhibit molecular mimicry of human proteins including steroid receptors, complement receptor, and integrin. Sequences for *T. mentagrophytes* were not retrieved from the protein databank. However, some fungi exhibit opioid-like sequences raising the chance that *T. mentagrophytes* might induce anti-dynorphin antibodies directly through molecular mimicry. Further study of larger samples may help to clarify the relationship between molecular mimicry, cross-reactive immunity for dynorphin, and combat-related PTSD.

Arg-Lys-Leu-Lys (SEQ ID NO: 1)

The majority of OCD, MDD, and dual diagnosis subjects demonstrated inhibition of binding to [³H]Dynorphin A 1–8 by Arg-Lys-Leu-Lys (SEQ ID NO: 1). Arg-Lys-Leu-Lys (SEQ ID NO: 1) is displayed by several organisms. However, its presence on Streptococcal proteins may be of clearest relevance to OCD which can occur during epitope-specific immunity for brain proteins. However, there is no established relationship between anti-dynorphin antibodies and the occurrence of OCD with Sydenham's chorea or influenza.

Arg-Lys-Leu-Lys (SEQ ID NO: 1) also is expressed by *P. falciparum*. Malaria had a high incidence among veterans of the South Pacific and Vietnam.

In addition to its expression by microbes, Arg-Lys-Leu-Lys (SEQ ID NO: 1) also is displayed by two groups of human proteins that have neuropharmacological function. First are proteins that regulate cellular calcium metabolism. Second are proteins that regulate metabolism of gamma-aminobutyric acid (GABA), a central neuromodulator. Abnormalities of these proteins result in disorders with clinical similarity to non-psychopathological aspects of psychiatric disorders and their treatment. Conceivably, the immune response for microbial Arg-Lys-Leu-Lys (SEQ ID NO: 1) can lead to reactivity for human Arg-Lys-Leu-Lys (SEQ ID NO: 1). Antibodies for Arg-Lys-Leu-Lys (SEQ ID NO: 1) might impair the function of human proteins that display the epitope. The presence of Arg-Lys-Leu-Lys (SEQ ID NO: 1) on microbial and human proteins can provide a window of opportunity for immunological attack on environmental antigen to mistakenly disable human regulatory proteins.

A sequence from a regulatory domain of brain calcium/calmodulin-dependent protein kinase that is shared with calmodulin binding proteins displays Arg-Lys-Leu-Lys (SEQ ID NO: 1). β-endorphin and dynorphin bind calmodulin. However, leucine-enkephalin does not bind calmodulin. This difference localizes calmodulin binding to Arg-Pro-Lys-Leu-Lys[13] (SEQ ID NO: 6) of dynorphin.

Arg-Lys-Leu-Lys (SEQ ID NO: 1) also comprises a portion of the binding site for the antipsychotic drug trifluoperazine (TFP) on skeletal and cardiac muscle calsequestrin, a protein that binds and stores calcium.

Homologous, but non-identical, sequences are present on the ryanodine receptor (Leu-Lys-Leu-Lys) (SEQ ID NO: 8). Ryanodine is a plant alkaloid that binds the calcium-release channel in muscle sarcoplasmic reticulum. Abnormalities of calcium release and the ryanodine receptor are linked to malignant hyperthermia. The disorder may be a consequence of an abnormal gene for the ryanodine receptor. Malignant hyperthermia (MH) occurs after exposure to some anesthetics, and is characterized by hyperpyrexia and skeletal muscle rigidity. Psychiatric patients are at risk to develop a disorder with similar symptoms, neuroleptic malignant syndrome (NMS). A relationship between NMS and MH is suggested by similarity in clinical features, abnormal in vitro skeletal muscle contractures to halothane, and response to dantrolene sodium, a skeletal muscle relaxant. Abnormal muscle biopsies identify patients at risk for both malignant hyperthermia and neuroleptic malignant syndrome. Immunity for homologous sequences from several proteins important to muscle physiology is of considerable interest since some patients with psychiatric disorders display abnormal muscle biopsies and abnormal neuromuscular function.

Proteins that regulate metabolism of gamma-aminobutyric acid (GABA) also display Arg-Lys-Leu-Lys (SEQ ID NO: 1). Arg-Lys-Leu-Lys (SEQ ID NO: 1) is present on glutamate decarboxylase (GAD). This is the rate-limiting enzyme for the conversion of glutamate, an excitotoxic neurotransmitter, to gamma aminobutyric acid (GABA). Several studies implicate alterations in glutamate in the pathogenesis of schizophrenia and Alzheimer's disease. Changes in central GABA relate to the occurrence of panic disorder, anxiety, and depression.

GAD is also present in pancreatic beta cells. Autoimmunity for GAD is implicated in insulin dependent diabetes mellitus and stiff-man syndrome, a neurological disorder characterized by progressive rigidity. Diabetes mellitus exhibits immunity for GAD. Anti-GAD antibodies are measurable early or late in the disease in patients with peripheral neuropathy. Anti-GAD may be predictive of susceptibility to IDDM.

Patients with stiff-man syndrome also exhibit antibodies for GAD in serum and CSF that bind GABA-ergic neurons and pancreatic beta cells. Consequently, there is a high incidence of insulin-dependent diabetes mellitus in stiff-man syndrome. Binding is detected to whole enzyme and the specific epitopes involved are not yet defined.

---

I claim:

1. A method for detecting in a sample of human body fluid antibodies reactive with *Staphylococcus aureus* REPB 275–290 and Arg-Lys-Leu-Lys (SEQ ID NO: 1) comprising the following steps:
   (a) coating a multiwell plate with a solution of *Staphylococcus aureus* REPB 275–290 and a solution of Arg-Lys-Leu-Lys (SEQ ID NO: 1), sealing said plate with an adhesive cover, incubating said plate for more than 24 hours with said solutions at about 0° to 4° C. followed by a blocking step;
   (b) allowing said sample of human body fluid to react with said coated plate, in humidified air containing about 5 to 7 percent $CO_2$ for about 1.5 to 3 hours at about 37° C.;
   (c) washing said plate with a buffered detergent more than 5 times to remove unbound material from said plate;
   (d) adding anti-human antibody conjugated with a marker entity to said washed plate of step (c) and, after sealing the plate with an adhesive cover, incubating the plate in humidified air containing about 5–7 percent $CO_2$ for about 1.5 to 3 hours at about 37° C. to allow conjugated-antibody to bind with human antibody bound to said neuropeptide;
   (e) removing unreacted material from said plate by washing more than 5 times;
   (f) detecting said marker entity and comparing with a control sample treated identically as in step (a) through step (e).

2. The method of claim 1, wherein said marker entity is selected from the group consisting of an enzyme, a fluorophore, or a radioisotope.

3. A kit for detecting in a sample of human body fluid antibodies reactive with antibodies reactive with *Staphylococcus aureus* REPB 275–290 and Arg-Lys-Leu-Lys (SEQ ID NO: 1) comprising:

1 or more microtiter plates, a solution of *Staphylococcus aureus* REPB 275–290, a solution of Arg-Lys-Leu-Lys (SEQ ID NO: 1), a labeled anti-human antibody, and reagents necessary to detect the labeled anti-human antibody.

4. The kit of claim 3 wherein the label of the labeled anti-human antibody is selected from the group consisting of an enzyme, a fluorophore, or a radioisotope.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Arg Lys Leu Lys
1

( 2 ) INFORMATION FOR SEQ ID NO:2:

( i ) SEQUENCE CHARACTERISTICS:
( A ) LENGTH: 16 amino acids
( B ) TYPE: amino acid
( D ) TOPOLOGY: linear ( i i ) MOLECULE TYPE: peptide ( x i ) SEQUENCE DESCRIPTION: SEQ ID NO:2:

Tyr Gly Gly Phe Leu Arg Arg Ile Arg Pro Lys Leu Lys Trp Asp Asn
1               5                   10                  15

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Tyr Gly Gly Leu Leu Lys Glu Ile His Lys Lys Leu Asn Leu Asp Asp
1               5                   10                  15

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Tyr Gly Gly Phe Leu
1               5

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Tyr Gly Gly Leu Leu
1               5

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Arg Pro Lys Leu Lys
1               5

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Arg Lys Ala Lys ( 2 ) INFORMATION FOR SEQ ID NO:8:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:8:

Leu Lys Leu Lys
   1

( 2 ) INFORMATION FOR SEQ ID NO:9:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:9:

Ile Arg Leu Arg
   1

( 2 ) INFORMATION FOR SEQ ID NO:10:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:10:

Gln Lys Ser Lys
   1